(12) United States Patent
Mock et al.

(10) Patent No.: US 11,273,294 B2
(45) Date of Patent: Mar. 15, 2022

(54) BALLOON CATHETER ASSEMBLY FOR INSERTION AND POSITIONING THERAPEUTIC DEVICES WITHIN A VASCULAR SYSTEM

(71) Applicants: STRYKER CORPORATION, Kalamazoo, MI (US); STRYKER EUROPEAN HOLDINGS I, LLC, Kalamazoo, MI (US)

(72) Inventors: Thomas J. Mock, Emeryville, CA (US); Alice Bradbury Welsh Brochu, Pleasanton, CA (US); Murtagh M. Murphy, Douglas (IE); Mariel E. Bolhouse, Mountain View, CA (US); David P. Marceau, Salt Lake City, UT (US)

(73) Assignee: Stryker Corporation, Kalamazoo, MI (US)

(*) Notice: Subject to any disclaimer, the term of this patent is extended or adjusted under 35 U.S.C. 154(b) by 182 days.

(21) Appl. No.: 16/440,360

(22) Filed: Jun. 13, 2019

(65) Prior Publication Data
US 2019/0381287 A1 Dec. 19, 2019

Related U.S. Application Data

(60) Provisional application No. 62/685,148, filed on Jun. 14, 2018.

(51) Int. Cl.
*A61M 25/10* (2013.01)

(52) U.S. Cl.
CPC .. *A61M 25/10182* (2013.11); *A61M 25/1002* (2013.01); *A61M 25/10184* (2013.11);
(Continued)

(58) Field of Classification Search
CPC .............. A61M 25/003; A61M 25/007; A61M 25/0075; A61M 25/10; A61M 25/1002;
(Continued)

(56) References Cited

U.S. PATENT DOCUMENTS 5,135,494 A * 8/1992 Engelson .......... A61M 25/0075
604/99.02
5,527,292 A 6/1996 Adams et al.
(Continued)

FOREIGN PATENT DOCUMENTS

DE 102013101338 8/2014
EP 0564747 10/1993

OTHER PUBLICATIONS

PCT International Search Report and Written Opinion for International Appln. No. PCT/US019/036982, dated Oct. 15, 2019 (16 pages).
(Continued)

*Primary Examiner* — Robert A Lynch
(74) *Attorney, Agent, or Firm* — Vista IP Law Group, LLP

(57) ABSTRACT

A balloon catheter which allows for faster preparation and more effective purging of air within the catheter, while also providing a more space efficient design, wherein the balloon catheter includes a tubular outer member and a tubular inner member disposed in the lumen of the outer member such that the outer member and inner member define an annular fluid path between them. A balloon is secured to and circumferentially surrounds an outer surface of the distal portion of the outer member. A tubular seal is disposed circumferentially around the inner surface of the distal portion of the outer member. The inner member is movable longitudinally relative to the outer member from a non-sealing position in which the annular fluid path is open, and a sealing position in which the distal portion of the inner member contacts the seal thereby sealing the annular fluid path at the seal.

10 Claims, 7 Drawing Sheets

(52) U.S. Cl.
CPC .................. *A61M 2025/109* (2013.01); *A61M 2025/1052* (2013.01); *A61M 2025/1077* (2013.01); *A61M 2205/0216* (2013.01)

(58) Field of Classification Search
CPC ........ A61M 25/1018; A61M 25/10182; A61M 25/10184; A61M 25/10185; A61M 25/1025; A61M 25/1027; A61M 25/1029; A61M 25/1034; A61M 25/1036; A61M 25/104; A61M 2025/0013; A61M 2025/0075; A61M 2025/1052; A61M 2025/1061; A61M 2025/1063; A61M 2025/1077; A61M 2025/109; A61M 2025/1093; A61M 2025/1095; A61M 2025/1097; A61M 2205/0216; A61F 2/958; A61B 17/12031; A61B 17/12036; A61B 17/1204; A61B 17/12099; A61B 17/12109; A61B 17/12118; A61B 17/12136; A61B 17/22032; A61B 17/221
See application file for complete search history.

(56) References Cited

U.S. PATENT DOCUMENTS

| | | | |
|---|---|---|---|
| 5,728,065 A * | 3/1998 | Follmer | A61M 25/10 604/96.01 |
| 6,638,245 B2 | 10/2003 | Miller et al. | |
| 7,736,355 B2 | 6/2010 | Itou et al. | |
| 7,972,294 B2 | 7/2011 | Nash et al. | |
| 8,048,032 B2 | 11/2011 | Root et al. | |
| 8,523,801 B2 | 9/2013 | Nash et al. | |
| RE45,776 E | 10/2015 | Root et al. | |
| 9,352,123 B2 | 5/2016 | Zhou et al. | |
| 9,433,427 B2 | 9/2016 | Look et al. | |
| 9,561,345 B2 | 2/2017 | Garrison et al. | |
| 9,681,882 B2 | 6/2017 | Garrison et al. | |
| 9,820,761 B2 | 11/2017 | Garrison | |
| 9,913,936 B2 | 3/2018 | Look et al. | |
| 2002/0198492 A1* | 12/2002 | Miller | A61M 25/10 604/96.01 |
| 2006/0036275 A1 | 2/2006 | Bagaoisan | |
| 2009/0264865 A1 | 10/2009 | Kawai | |
| 2012/0004529 A1* | 1/2012 | Tolkowsky | G06T 7/00 600/407 |
| 2012/0265135 A1* | 10/2012 | Porter | A61M 25/10 604/103.05 |
| 2013/0197432 A1* | 8/2013 | Von Oepen | A61F 2/958 604/96.01 |
| 2014/0371672 A1 | 12/2014 | Pinchuk et al. | |

OTHER PUBLICATIONS

PCT International Preliminary Report on Patentability (Chapter 1 of the Patent Cooperation Treaty) for PCT/US201 9/036982, dated Dec. 24, 2020 (11 pages).

* cited by examiner

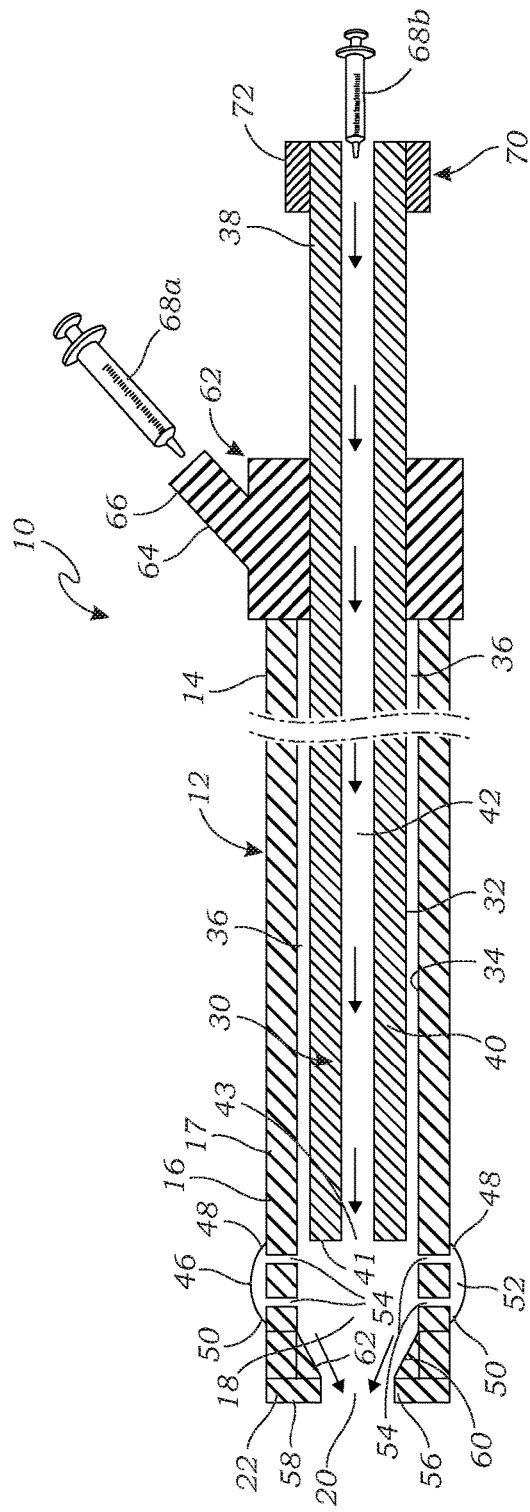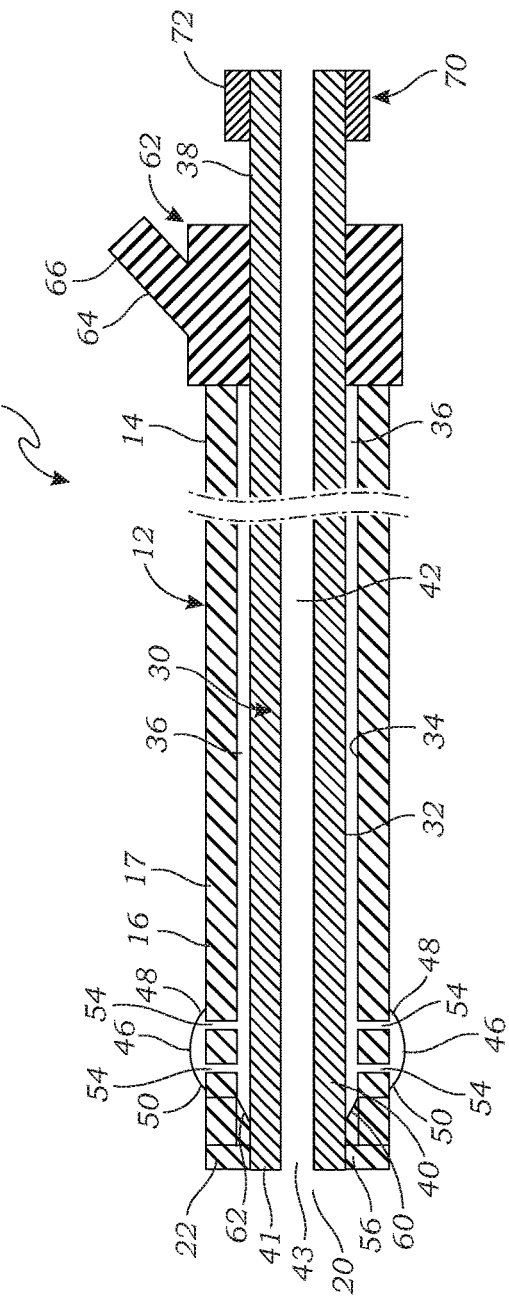

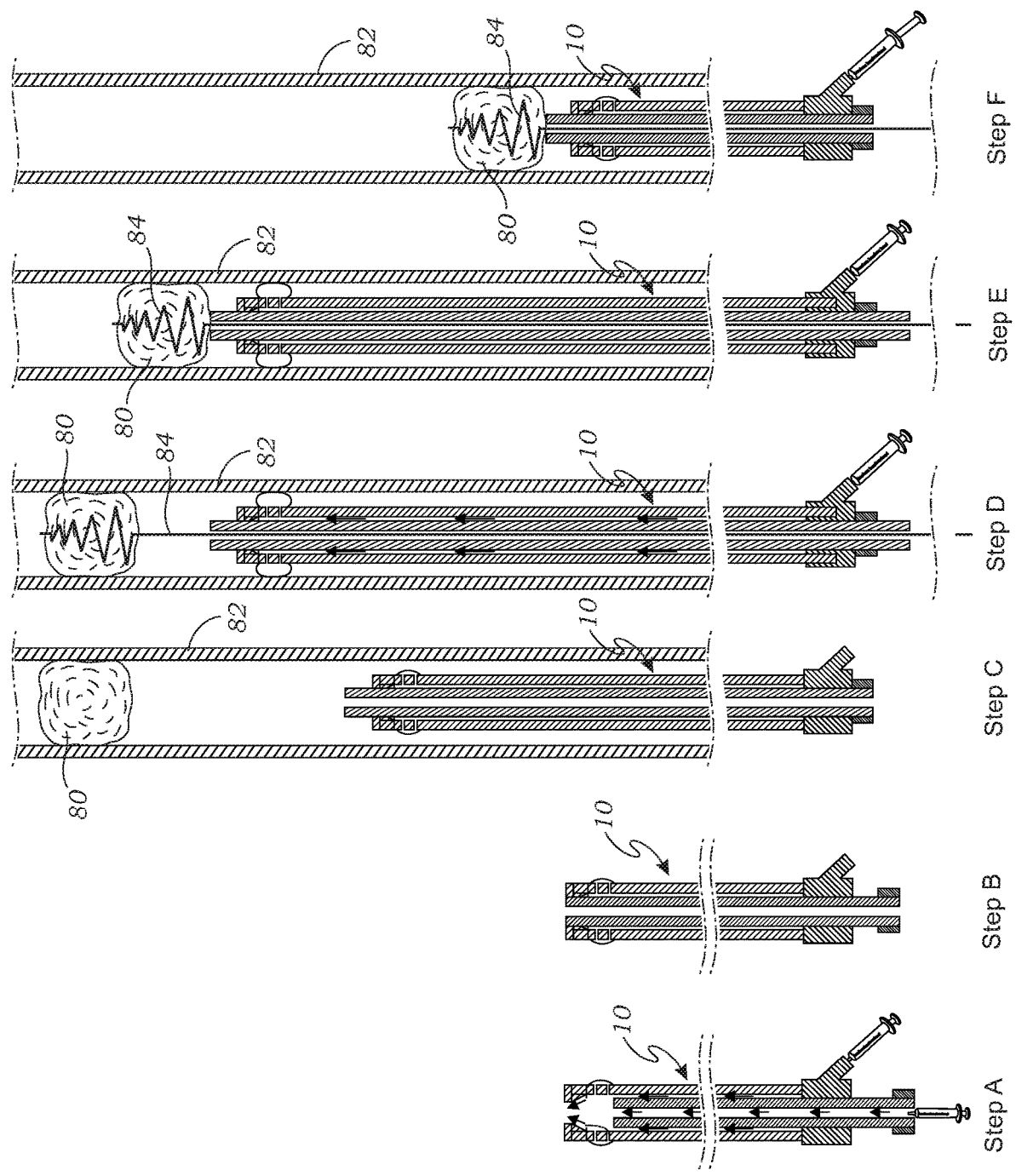

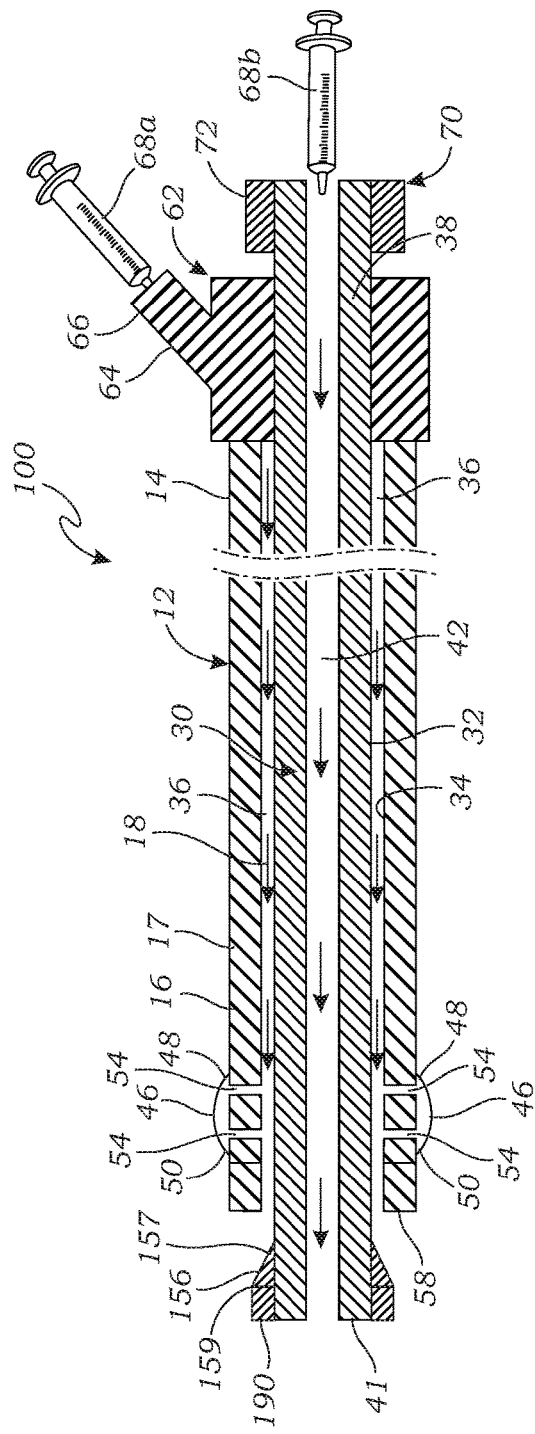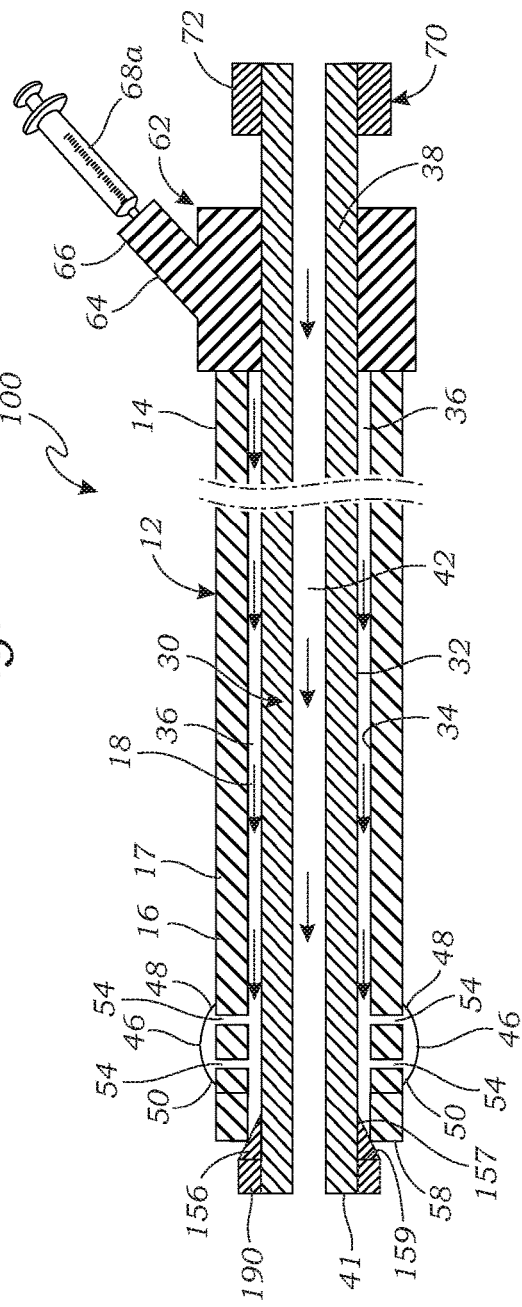

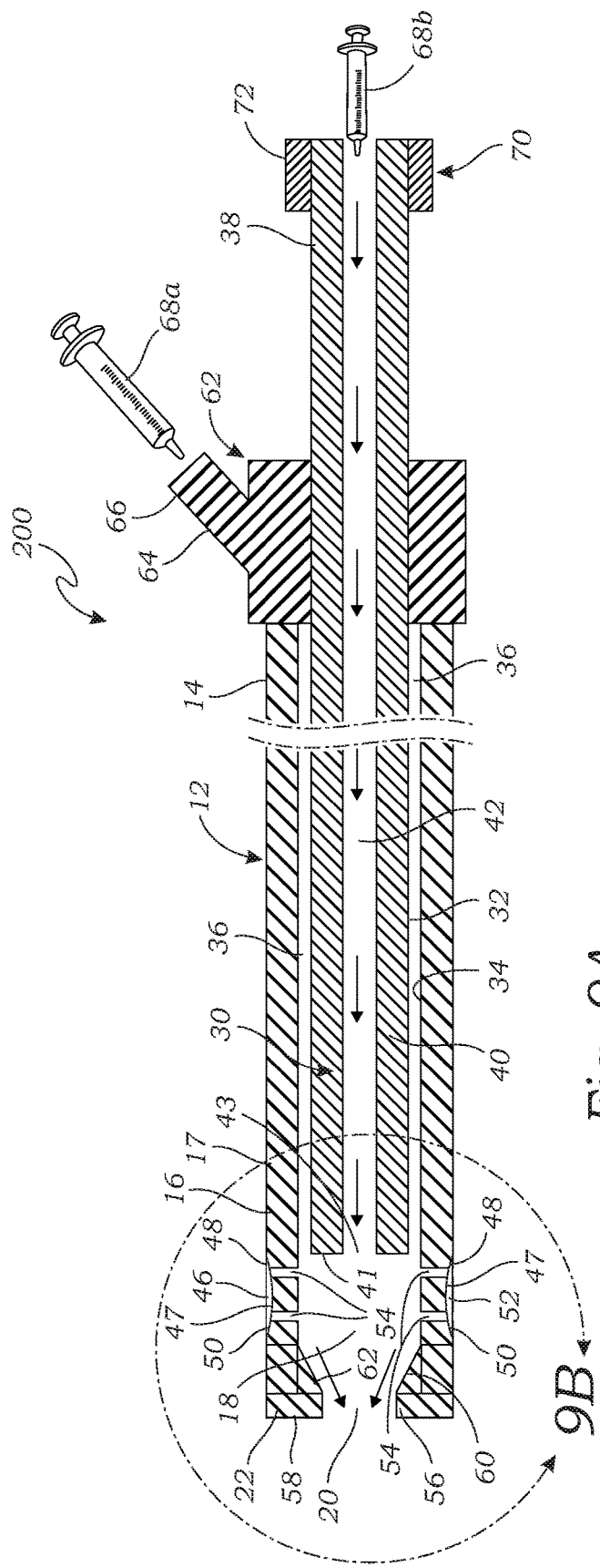
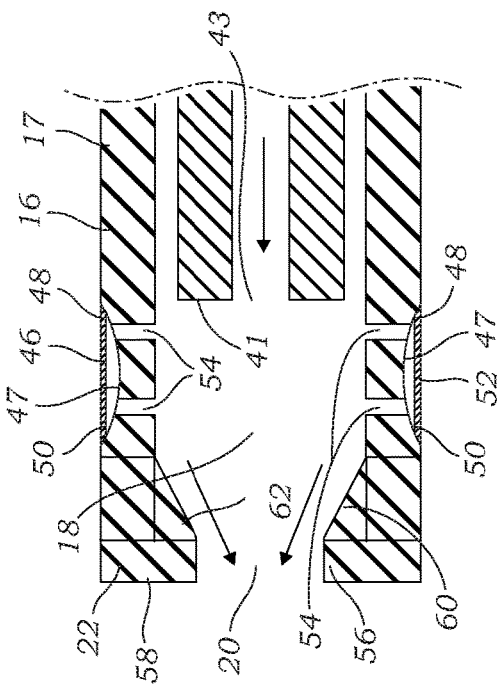
Fig. 9A
Fig. 9B

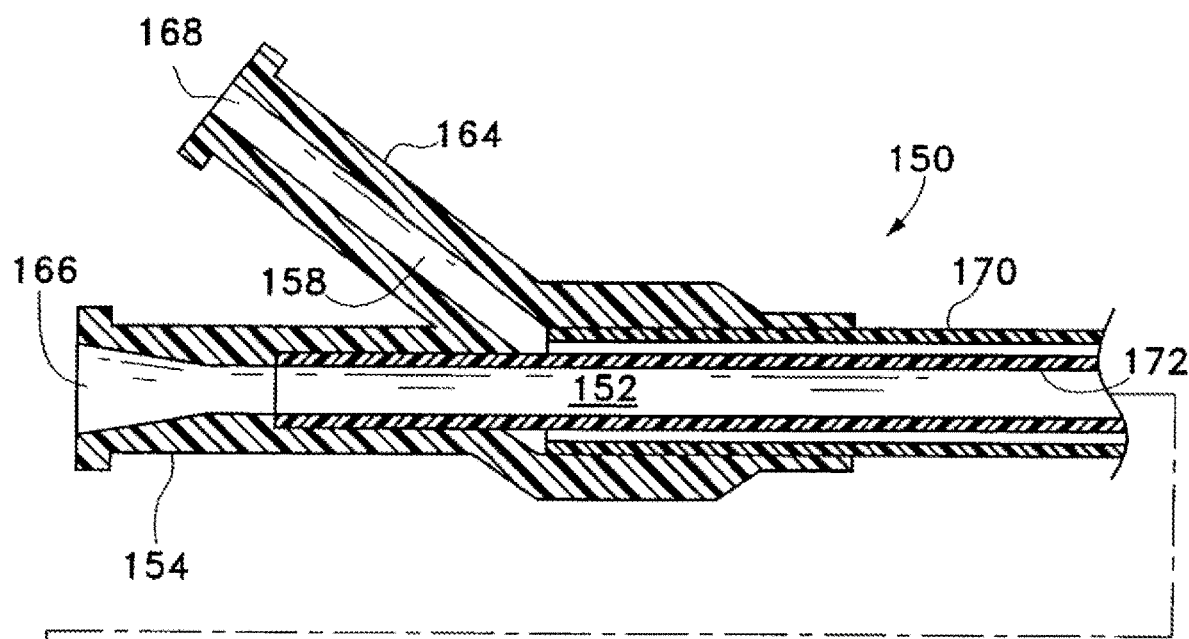
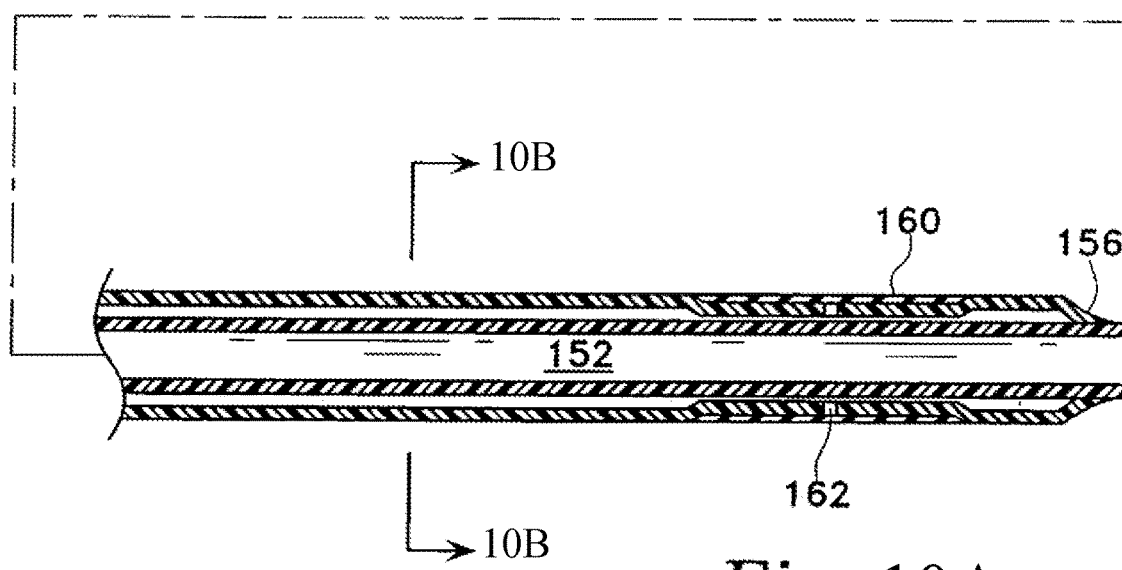
Fig. 10A
*Prior ART*
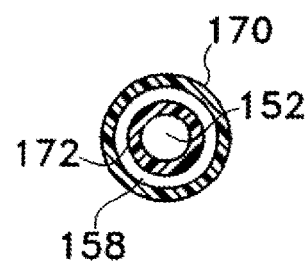
*Prior ART*
*Fig. 10B*

BALLOON CATHETER ASSEMBLY FOR INSERTION AND POSITIONING THERAPEUTIC DEVICES WITHIN A VASCULAR SYSTEM

RELATED APPLICATION DATA

The present application claims the benefit, under 35 U.S.C. Section 119, 120, and any other applicable laws, to U.S. provisional Application No. 62/685,148 filed on Jun. 14, 2018. The foregoing application is hereby incorporated by reference herein in its entirety.

FIELD OF THE INVENTION

The present invention generally relates to medical devices and methods for performing procedures within a lumen of a vascular system of a patient, and more particularly, to devices and methods for performing a procedure with a balloon guide catheter within a vascular system, such as treating ischemic strokes, and blocking or restricting blood flow for other treatment or diagnostic purposes.

BACKGROUND

Various designs of medical catheters have been previously provided for performing a variety of medical procedures, including interventional therapy, drug delivery, diagnosis, perfusion, and the like. In general, medical catheters are used by introducing the catheter through an entry site of a patient and into the vascular system of the patient, such as a vein or artery. The catheter is advanced from the entry site by guiding and pushing the catheter through the vascular system to a target site for performing a therapeutic and/or diagnostic medical procedure.

An example of one type of intravascular catheter is a balloon catheter which includes an elongated tubular member and a balloon affixed to the tubular member, for example, to a distal portion of the tubular member or other suitable location. The tubular member includes an inflation lumen extending from a proximal end of the tubular member to the balloon for injecting fluid into the balloon to inflate the balloon. Various types of balloon catheters have been previously disclosed for performing a variety of different medical procedures. For instance, balloon catheters for diagnosing and treating neurological disorders, such as ischemic stroke, is disclosed in U.S. Pat. No. 6,638,245 (the '245 patent), the disclosure of which is fully incorporated herein. FIGS. 10A and 10B illustrate a prior art balloon guide catheter 150, as disclosed in the '245 patent. The balloon catheter 150 comprises an outer tubular member 170 and an inner tubular member 172 within the outer tubular member 170. The balloon catheter 150 has an inflatable balloon 160 disposed on the distal end of the outer tubular member 160. The annular space between the outer tubular member 170 and the inner tubular member 172 forms a fluid supply lumen 158 for inflating the balloon 160. The balloon catheter 150 is advanced to a target site within the vascular system of a patient through an introducer sheath. Once in place, treatment catheters may be advanced to the target site through the working lumen 152 of the inner tubular member 172. Accordingly, the prior balloon catheters, such as the balloon catheter 150, required at least three catheter shaft thicknesses (the combined thicknesses of the outer tubular member 170, the inner tubular member 172 and the introducer sheath). Thus, the prior balloon catheter must accommodate three catheter shafts, which can restrict the diameter of the working lumen in order to make the outer diameter of the balloon guide catheter small enough to fit into the vessels of a vasculature system, especially when used small vessels such as the neurovascular system.

The use of balloon catheters in the neurological vasculature presents a number of catheter design challenges. For one, the blood vessels in the brain are typically very small in diameter, as small as several millimeters or less, requiring that a catheter advanced into these blood vessels have an outside diameter as small as one French (0.33 mm). Furthermore, the brain vasculature is highly tortuous, requiring that a neurological catheter be very flexible, especially at the distal end, to travel through and conform to the tortuous path. Also, the blood vessels of the brain are quite fragile, so a neurological catheter must have a smooth, non-traumatic periphery.

Balloon catheters generally require preparation prior to use in advancing the catheter into the vasculature of a patient by purging air out of the catheter. As described above, a balloon catheter typically has an elongated tube and an inflation lumen. In some cases, a balloon catheter may also have multiple tubes (e.g., concentric tubes with an inner tube disposed within an outer tube). Each of these structures, including the tube(s), inflation lumen, and balloon must be purged of air with a fluid (e.g., saline) prior to advancing the catheter through the vasculature of the patient to prevent air from being introduced into the patient which can cause embolisms or other trauma in the patient. However, due to the closed-end fluid path from the inflation lumen to the balloon, and in many cases, within the tube(s) of the catheter, it is difficult and very time-consuming to purge all of the air from system. It is also difficult to determine when all of the air has been purged from the catheter because of the closed-end fluid paths. As a result, purging the air from prior balloon catheters during preparation for surgery often takes up to 15 minutes, and even then, the purging is not always successful.

SUMMARY

The present invention is directed to a balloon guide catheter having an innovative configuration which allows for faster preparation and more effective purging of air within the catheter (and filling the catheter with fluid, such as saline) than previously known balloon catheters. The presently disclosed balloon guide catheter is useful for insertion and positioning of therapeutic devices within a vascular system of a patient. For instance, the balloon guide catheter is particularly useful in imaging, diagnosing and/or treating blockages of a blood vessel, such as coronary occlusion or ischemic strokes. An ischemic stroke is caused by the blockage of a blood vessel in the brain, either by the narrowing of the blood vessel or presence of an embolus (e.g., a thrombus, or other abnormal material in the blood vessel). The balloon guide catheter of the present invention is also particularly well-suited for use in the neurological vasculature because it can be adjusted to have a more flexible distal end.

As explained above, balloon catheters typically require preparation of purging air from the system before advancing the catheter into the vasculature of a patient. The balloon guide catheter of the present invention is adjustable from a purging configuration in which the lumens of the tubular members and inflation lumen for inflating the balloon have an open-ended fluid path and an inflation configuration in which the inflation lumen is sealed so that the pressurized fluid can be injected into the inflation lumen to inflate the balloon.

In a first embodiment, a balloon guide catheter according to the present invention comprises an elongated, flexible, tubular outer member having a proximal portion, a distal portion, and an outer member lumen extending there between. The outer member lumen is in communication with a distal opening of the outer member. An elongated, flexible, tubular inner member is disposed at least partially within the outer member lumen such that an outer surface of the inner member and an inner surface of the outer member together define an annular fluid path between the inner member and the outer member. The inner member may be a delivery/treatment catheter. The inner member has a proximal portion, a distal portion, and an inner member lumen extending there between. The inner member lumen is in communication with a distal opening of the inner member.

A balloon is secured to the outer member. The balloon can be secured to any suitable portion of the outer member, including but not limited to the distal portion. The balloon comprises an elastomeric member having respective proximal and distal ends. The proximal and distal ends of the balloon are secured to and circumferentially around an outer surface of the distal portion of the outer member such that an inner surface of the elastomeric member and an outer surface of the outer member define an inflatable balloon interior. The outer member has one or more passages through a wall of the outer member that form a fluid pathway between the annular fluid path and the balloon interior.

An elastomeric tubular seal is disposed circumferentially around the outer member distal of the one or more passages through the wall of the outer member. For example, the tubular seal may be disposed circumferentially around the inner surface of the distal portion of the outer member, or other suitable sealing configuration. The seal may be secured proximal to the distal end of the outer member. The seal is configured to form a fluid-tight seal between the inner surface of the outer member and the outer surface of the inner member, such that it seals the annular fluid path when the inner member is in a sealing position.

The inner member is movable longitudinally relative to the outer member from a non-sealing position in which the distal portion of the inner member is positioned proximal of the seal, and a sealing position in which the distal portion of the inner member contacts the seal thereby sealing the annular fluid path at the location of the seal. In other words, the inner member can telescope within the outer member between the sealing position and the non-sealing position. The relative movement may be accomplished by moving the inner member, or by moving the outer member, such that there is longitudinal relative movement between the inner member and the outer member.

Accordingly, as the annular space between outer member and the inner member form the inflation lumen for the balloon, the balloon guide catheter of the present invention only requires two shafts, and therefore only two shaft thicknesses, to perform the same functions as the prior art balloon catheter having three shafts (as described above). This provides a very advantageous space efficiency, allowing the inner working lumen of the balloon guide catheter to be larger than previously disclosed balloon catheters, for a given outer diameter of the balloon guide catheter.

In another aspect of the balloon guide catheter, the seal and the inner member may be configured such that the inner member may be moved distally through the seal such that the distal portion of the inner member is positioned distally of the seal, while the seal continues to seal the annular fluid path. This movement can occur outside the body or in tortuous vasculature. In this way, the distal portion of the inner member may extend distally past the distal end of the outer member and the balloon, thereby providing a more flexible distal end of the guide catheter assembly. This can be useful in guiding the catheter through the vascular system of the patient.

In another aspect of the present invention, when the inner member is in the non-sealing position (i.e., when the distal portion of the inner member is positioned proximal of the seal), air may be purged from the balloon guide catheter by introducing pressurized fluid through the respective outer member lumen and inner member lumen such that fluid flows through the lumens and fluid paths of the catheter and out through the inner member distal opening and the outer member distal opening. More specifically, air is purged from one or more of the outer member lumen, inner member lumen, annular fluid path, one or more passages, and balloon interior, respectively, by introducing pressurized fluid through the respective outer member lumen and inner member lumen such that fluid flows through the one or more of the outer member lumen, inner member lumen, annular fluid path, one or more passages, and balloon interior and out through the inner member distal opening and the outer member distal opening. This allows an open-ended flow path for introducing fluid into the catheter to purge air from the catheter. Hence, a user can confirm that air has been successfully been purged from the catheter by observing fluid flow out through the inner member distal opening and the outer member distal opening.

In still another aspect, when the inner member is in the sealing position, pressurized fluid introduced into the proximal portion of the outer member lumen flows through the annular fluid path and the one or more passages, respectively, into the balloon interior to thereby inflate the balloon. The seal is located distal of the inflation passages in the wall of the outer member. Hence, when the inner member is in the sealing position, the annular fluid path is sealed at a location distal of the inflation passages such that pressurized fluid injected into annular fluid path at the proximal portion of the outer member injects pressurized fluid into the balloon through the inflation passages.

Another embodiment of the present invention is directed to a method of using the first embodiment of the balloon guide catheter. The method comprises preparing the balloon guide catheter for insertion into the vascular system of the patient by purging air from the guide catheter with the inner member positioned in the non-sealing position. The inner member may be pre-positioned in the non-sealing position, or the inner member may be moved relative to the outer member to position the inner member in the non-sealing position. Air is purged from one or more of the outer member lumen, inner member lumen, one or more passages, annular flow path and balloon by introducing fluid through the inner member lumen and outer member lumen and observing fluid flowing out through the inner member distal opening and the outer member distal opening. When fluid is observed flowing out of the inner member distal opening and outer member distal opening, without air bubbles, the user can be assured that the balloon guide catheter has been purged of air.

The balloon guide catheter is inserted into the vascular system of the patient. As described herein, the balloon guide catheter may be inserted through an entry incision into an entry blood vessel, such as the inferior vena cava or femoral artery near the groin. The inner member and outer member are then advanced through the vascular system to position the balloon at a treatment site. The inner member and outer member may be advanced simultaneously, or separately, and at the same rate or different rates.

With the balloon positioned at the treatment site, the balloon is inflated. With the inner member positioned in the sealing position, the balloon is inflated by introducing fluid into the outer member lumen such that the fluid flows through the annular fluid path, through the one or more passages, and into the inflatable balloon interior. The balloon may be inflated within the blood vessel such that the balloon seals the blood vessel. This isolates the blood vessel downstream of the balloon from the flow of blood. A treatment procedure, such as imaging, embolus removal, intravascular device implantation, or the like may then be performed. For example, an imaging catheter may be inserted through the inner member and advanced past the distal end of the inner member to image the blood vessel or surrounding tissue. In the case of removing an embolus, such as in the treatment of an ischemic stroke, an embolus removal device may be inserted through the inner member, and advanced past the distal end of the inner member to grasp or otherwise capture the annulus, and remove the embolus from the blood vessel.

In additional aspects, the method may include the steps of moving the inner member from the non-sealing position to the sealing position, and/or from the sealing position to the non-sealing position.

In yet another aspect of the method, the inner member may be moved relative to the outer member such that the distal portion of the inner member extends through the seal and beyond a distal end of the outer member. This provides a more flexible tip to the balloon guide catheter for guiding and advancing the catheter through the vascular system. The inner member may be advanced to extend the distal portion of the inner member beyond the distal end of the outer member before or during the steps of inserting the inner member and outer member into the vascular system and advancing the inner member and outer member through the vascular system. The inner member may be advanced to extend the distal portion of the inner member prior to or after inflating the balloon while not impacting the balloon. The inner member may be advanced proximal to the seal to allow for a fast deflation of the balloon and completely removed from the vasculature while leave the outer member in place.

A second embodiment of a balloon guide catheter according to the present invention is similar to the first embodiment described above, except that the seal is disposed circumferentially around an outside surface of the distal portion of the inner member, instead of on the inside surface of the outer member. In the second embodiment, the balloon guide catheter comprises an elongated, flexible, tubular outer member having a proximal portion and a distal portion, and an outer member lumen extending therebetween. The outer member lumen is in fluid communication with a distal opening of the outer member. An elongated, flexible, tubular inner member is disposed at least partially within the outer member such that an outside surface of the inner member and inside surface of the outer member together define an annular fluid path. The inner member has a proximal portion, a distal portion, and an inner member lumen extending therebetween. The inner member lumen is in communication with a distal opening of the inner member.

A balloon is secured to the outer member, for example, at the distal portion of the outer member. The balloon comprises an elastomeric member having respective proximal and distal ends secured to and circumferentially around an outer surface of the distal portion of the outer member such that an inner surface of the elastomeric member and outer surface of the outer member define an inflatable balloon interior. The outer member has one or more passages through a wall of the outer member that form a fluid pathway between the annular fluid path and the balloon interior thereby inflating the balloon;

An elastomeric, tubular seal is disposed circumferentially around an outside surface of the distal portion of the inner member. The seal is configured to form a fluid tight seal between an inside surface of the outer member and the outer surface of the inner member.

The inner member is movable longitudinally relative to the outer member from a non-sealing position in which the seal is positioned distal to the outer member distal opening, and a sealing position in which the seal is positioned within the outer member lumen such that the seal contacts the inner surface of the outer member thereby sealing the annular fluid path. Said another way, the inner member can telescope within the outer member between the non-sealing position and the sealing position.

In another aspect of the second embodiment of the balloon guide catheter, the inner member may further include a distal stop on a distal end of the inner member located distal of a distal end of the outer member such that the stop prevents the distal end of the inner member from being moved proximally past the distal end of the outer member.

In still another aspect of the second embodiment, the seal and inner member are configured such when the inner member in the non-sealing position, air may be purged from one or more of the inner member lumen, outer member lumen, annular fluid path, one or more passages, and balloon by introducing fluid through the one or more of the inner member lumen outer member lumen, annular fluid path, one or more passages and balloon and out through the inner member distal opening and the outer member distal opening.

In still another feature of the second embodiment, the seal and the inner member are configured such that when the inner member is in the sealing position, fluid introduced into the outer member lumen flows through the annular fluid path, through the one or more passages and into the inflatable balloon interior, thereby inflating the balloon.

In still another aspect, the seal and the inner member may be configured such that at least a part of the distal portion of the inner member may be advanced distally past a distal end of the outer member to form a flexible, distal guide portion of the guide catheter. For example, a length may extend past the distal end of the outer member and can be selected by the physician on a case-by-case basis, such as a length of about one, two, three, four or more times a length of the balloon.

Another embodiment of the present invention is directed to a method of using the second embodiment of the balloon guide catheter. The method is similar to the method of using the first embodiment, except that the process of moving the inner member between the sealing and non-sealing positions is slightly different. The method comprises preparing the balloon guide catheter for insertion into the vascular system of the patient by purging air from the guide catheter with the inner member positioned in the non-sealing position, i.e., the seal positioned distal of the outer member outlet. The inner member may be pre-positioned in the sealing position, or the inner member may be moved relative to the outer member to position the inner member in the sealing position. Air is purged from one or more of the outer member lumen, inner member lumen, one or more passages, annular flow path and balloon by introducing fluid through the inner member lumen and outer member lumen and observing fluid flowing out through the inner member distal opening and the outer member distal opening. When fluid is observed flowing out of the inner member distal opening and outer member distal opening, without air bubbles, the balloon guide catheter has successfully been purged of air.

The balloon guide catheter is inserted into the vascular system of the patient. As described herein, the balloon guide catheter may be inserted through an entry incision into an entry blood vessel, such as the inferior vena cava or femoral artery near the groin. The inner member and outer member are then advanced through the vascular system to position the balloon at a treatment site. The inner member and outer member may be advanced simultaneously, or separately, and at the same rate or different rates.

With the balloon positioned at the treatment site, the balloon is inflated. With the inner member positioned in the sealing position (i.e., the seal positioned within the outer member outlet such that the seal contacts the inner surface of the outer member to seal the annular fluid path), the balloon is inflated by introducing fluid into the outer member lumen such that the fluid flows through the annular fluid path, through the one or more passages, and into the inflatable balloon interior. The remainder of procedure for using the second embodiment is the same as that described above for the first embodiment.

In additional aspects, the method of using the second embodiment of the balloon guide catheter may include the steps of moving the inner member from the non-sealing position to the sealing position, and/or from the sealing position to the non-sealing position.

In yet another aspect of the method, the inner member may be moved relative to the outer member such that the distal portion of the inner member extends beyond a distal end of the outer member to provide a flexible guide portion. This provides a more flexible tip to the balloon guide catheter for guiding and advancing the catheter through the vascular system. The inner member may be advanced to extend the distal portion of the inner member beyond the distal end of the outer member before or during the steps of inserting the inner member and outer member into the vascular system and advancing the inner member and outer member through the vascular system.

In additional aspects, the balloon guide catheter described herein may be used for additional applications beyond a guide catheter. The balloon catheter described herein may be used in any suitable application for a balloon catheter, including performing diagnostic or therapeutic procedures, with or without guiding another catheter using the balloon catheter.

In addition, the balloon catheter described herein may also be configured as a microcatheter for use in any suitable balloon microcatheter application. For instance, the balloon microcatheter has all of the structure and features of the balloon guide catheter described herein, wherein its components, such as the outer member, inner member and balloon, are sized and configured for advancement into small vessels of the vascular system. For example, the balloon microcatheter may be made of components which are more flexible and smaller than a typical balloon guide catheter, such as having an outside diameter (outer diameter of the outer member) of from 0.095 inches and 0.125 inches and an inside diameter (inner diameter of the inner member) of from 0.060 inches to 0.095 inches. For instance, a balloon guide catheter of this size may be useful in performing a thrombectomy aspiration. Moreover, for use within very small vessels, such as the smaller vessels within the neurovascular, the outer diameter of the outer member is from 0.027 inches to 0.037 inches and the inner diameter of the inner member is from 0.016 inches and 0.026 inches. Accordingly, the balloon microcatheter may be advanced into very small vessels of the vascular system, such as within the neurovascular, cardiovascular, or other small vessels.

Accordingly, embodiments described herein provide an innovative balloon guide catheter and methods of using the same which allow for faster preparation and more effective purging of air within the catheter than prior balloon catheters.

BRIEF DESCRIPTION OF THE DRAWINGS

The foregoing and other aspects of embodiments are described in further detail with reference to the accompanying drawings, wherein like reference numerals refer to like elements and the description for like elements shall be applicable for all described embodiments wherever relevant:

FIG. 1 is a side, cross-sectional view of a balloon guide catheter, with the inner member in the non-sealing position, according to one embodiment of the present invention;

FIG. 2 is a side, cross-sectional view of the balloon guide catheter of FIG. 1, with the inner member in the sealing position, according to one embodiment of the present invention;

FIG. 6 is a side cross-sectional view showing a procedure for using the balloon guide catheter of FIG. 1, according to one embodiment of the present invention;

FIG. 7 is a side, cross-sectional view of a balloon guide catheter, with the inner member in the non-sealing position, according to another embodiment of the present invention;

FIG. 8 is a side, cross-sectional view of the balloon guide catheter of FIG. 6, with the inner member in the sealing position, according to one embodiment of the present invention.

FIGS. 9A-9B illustrate a side, cross-sectional view of a balloon guide catheter, with the inner member in the non-sealing position, according to one embodiment of the present invention.

FIGS. 10A-10B illustrate a side, cross-sectional view of a prior art balloon guide catheter, as disclosed in the U.S. Pat. No. 6,638,245.

DETAILED DESCRIPTION

Figure 3:
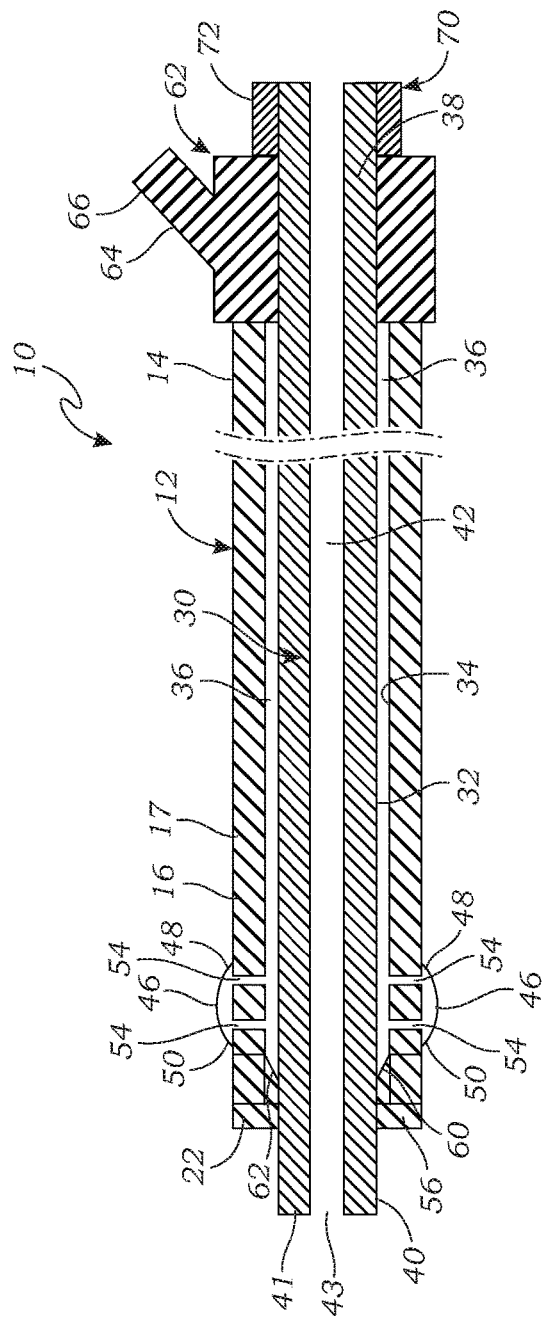
FIG. 3 is a side, cross-sectional view of the balloon guide catheter of FIG. 1, with the distal portion of the inner member extended beyond the distal end of the outer member, according to one embodiment of the present invention.

FIGS. 1-4 illustrate a balloon guide catheter 10 for performing a procedure within a vascular system, such as treating ischemic strokes, and blocking or restricting blood flow for other treatment or diagnostic purposes use in performing. The balloon guide catheter 10 is specially configured to allow for fast preparation for performing a surgical procedure using the catheter 10, including providing for fast and effective purging of air from the catheter 10.

The balloon guide catheter 10 includes an elongated, flexible, tubular outer member 12. The outer member 12 has a proximal portion 14, a distal portion 16, and an outer member lumen 18 extending between the proximal portion 14 and the distal portion 16. The outer member lumen 18 is in fluid communication with a distal opening 20 at the distal end 22 of the outer member 12.

The outer member 12 may be made of a polymeric tube, or other suitable material. The outer member 12 may also have one or more reinforcing members to provide reinforced and/or stiffened portions of the outer member 12. For example, a coil, braid, ribbon, hypotube or other structural member may be disposed on the inside, on the outside, and/or embedded within the wall of the outer member along a predetermined portion of the outer member 12. The reinforcing member may be made of any suitable material, such as a super-elastic alloy or shape-memory material to provide a specific shape to the reinforced portion of the outer member 12 under certain conditions.

An elongated, flexible, tubular inner member 30 is disposed within the outer member lumen 18. The inner member 30 is slidable longitudinally within, and relative to, the outer member 12. The inner member 30 has a proximal portion 38, a distal portion 40, and an inner member lumen 42 extending between the proximal portion 38 and the distal portion 40. The inner member lumen 42 is in fluid communication with a distal opening 43 of the inner member 30. Like the outer member 12, the inner member 30 may be made of a polymeric tube, or other suitable material, and may also have one or more reinforcing members to provide reinforced and/or stiffened portions of the inner member 10. The reinforcing members may be a coil, braid, ribbon, hypotube or other structural member disposed on the inside or on the outside and/or embedded within the wall of the inner member along a predetermined portion of the inner member 30. The reinforcing member may be made of any suitable material, such as a super-elastic alloy or shape-memory material to provide a specific shape to the reinforced portion of the outer member 12 under certain conditions.

The outer surface 32 of the inner member 30 and the inner surface 34 of the outer member define an annular fluid path 36 between the inner member 30 and the outer member 12. The inner member lumen 42 is in communication with a distal opening 44 of the inner member 30.

The balloon guide catheter 10 has balloon 46 secured to the outer member 12 at the distal portion 16 of the outer member 12. It should be understood that the balloon 46 may be located at any suitable location on the outer member 12, such as proximal to the distal portion 16, in the middle portion of the outer member 12, etc. The balloon 46 is formed of an elastomeric member and has a proximal end 48 and a distal end 50. While the balloon 46 may be secured to the outer member 12 in various ways, in this described embodiment the proximal end 48 and distal end 50 of the balloon 46 are secured to and circumferentially disposed around the outer surface 17 of the distal portion 16 of the outer member 12. Thus, the inner surface of the elastomeric member and the outer surface 17 of the outer member 12 define an inflatable balloon interior 52. The outer member 12 has one or more conduits or passages 54 through the wall of the outer member 12 that form a fluid pathway between the annular fluid path 36 and the balloon interior 52.

An elastomeric, tubular seal 56 is disposed on the outer member 12 proximate the distal end 22 of the outer member 12, such that it is distal of the one or more passages 54. The seal 56 may be configured in various ways on the outer member 12, so long as it forms a fluid tight seal around the inner member 30 when the inner member 30 is positioned within the seal 56, i.e., when the inner member 30 is positioned with the distal portion 40 of the inner member 30 within the seal 56. As depicted in the embodiment of FIGS. 1-4, a distal seal portion 58 is disposed on the distal end 22 of the outer member 12 and a proximal seal portion 60 is disposed circumferentially around the inner surface 34 of the distal portion 16 of the outer member 12. The proximal seal portion 60 may have a tapered inside surface which tapers inward from the proximal end of proximal seal portion 60 to the inner most part of the seal 56. The tapered inside surface 62 helps guide and assist the inner member 30 through the seal 56 the inner member 30 is moved from a position in which the distal end 41 of the inner member 30 is proximal of the seal 56 to a position with the distal portion 40 within the seal 56. Accordingly, the seal 56 is configured to form a fluid tight seal between the inner surface 34 of the outer member 12 and the outer surface 32 of the inner member 30 such that the seal 56 seals the annular fluid path 36 when the inner member 30 is in a sealing position (see FIG. 3).

The inner member 30 is slidable relative to the outer member 12 from a non-sealing position (as shown in FIG. 1) to a sealing position (as shown in FIG. 2 and FIG. 3). The relative movement may be accomplished by moving the inner member 30, or by moving the outer member 12, or by moving both, such that there is longitudinal relative movement between the inner member 30 and the outer member 12. However, in most uses, when adjusting the catheter 10 from the sealing position to the non-sealing position, the inner member 30 will be moved while the outer member 12 remains stationary.

As shown in FIG. 1, in the non-sealing position of the inner member 30, the distal end 41 (and distal portion 40) of the inner member 30 is positioned proximal of the seal 56 such that the inner member 30 is not in contact with the seal 56. Turning to FIG. 2, the inner member 30 has been moved longitudinally relative to the outer member 12 to the sealing position by sliding the inner member 30 within the outer member 12, such that the distal portion 40 of the inner member 30 is positioned within the seal 56 such that the distal portion 40 contacts the seal 56. When the inner member 30 is in the sealing position, the seal 56 seals the annular fluid path 36 at the location of the seal 56.

The balloon guide catheter 10 may also include a hub 62 secured to the proximal portion 14 of the outer member 12. The hub 62 has a fluid port 64 in fluid communication with only the outer member lumen 18 (i.e., isolated from the inner member lumen 42) for inserting fluid into, or extracting fluid from, the outer member lumen 18. For example, the fluid port 64 may have a female Luer lock 66 for attaching a syringe 68 or other fluid source having a mating male Luer lock.

The balloon guide catheter 10 may also have a fluid interface 70 secured to the proximal portion 38 of the inner member 30. The fluid interface 70 may have an opening in fluid communication with only the inner member lumen 42 (i.e., isolated from the outer member lumen 18) for inserting fluid into, or extracting fluid from, the inner member lumen 42. For instance, the fluid interface 70 may have a female Luer lock 72 for attaching a syringe 68 or other fluid source having a mating male Luer lock.

Turning to FIG. 3, the balloon guide catheter 10 is shown with the inner member 30 moved distally further than in FIG. 2, such that the distal portion 40 of the inner member 30 extends distally past the seal 56 and the distal end 22 of the outer member 12. The seal 56 and the inner member 30 are configured such that the inner member 30 may be moved distally through the seal 56 while the seal 56 maintains the fluid tight seal of the annular fluid path 36. In other words, the inner member 30 is telescoped relative to the outer member 12, or the inner member 30 can telescope relative to the outer member 12. This arrangement of the balloon guide catheter 10 provides a more flexible distal end of the guide catheter assembly 10, especially since the distal portion 16 of the outer member 12 with the balloon 46 attached can be relatively stiff and inflexible. The more flexible distal tip can make it easier to guide and manipulate the catheter 10 through vascular system, especially tortuous regions of the vascular system, such as the neurovascular.

Referring again to FIG. 1, with the inner member 30 in the non-sealing position, air may be easily purged from the balloon guide catheter 10 because there is an open fluid pathway from the proximal portions 38, 14 and the distal openings 43, 20 of the inner member 30 and outer member 12, respectively. Air is purged from the balloon guide catheter 10 by introducing pressurized fluid through the outer member lumen 18 via the fluid port 64 of the hub 62 and through the inner member lumen 42 via the fluid interface 70. As shown in FIG. 1, the syringe 68a filled with fluid, such as saline, is attached to the Luer lock 66 of the fluid port 64. The syringe 68a is then used to inject pressurized fluid into the outer member lumen 18 such that fluid flows through the annular fluid path 36, the outer member lumen 18, the passages 54, the balloon 46 and out through the outer member distal opening 20. Similarly, the syringe 68b filled with fluid, such as saline, is attached to the Luer lock 72 of the fluid interface 70. The syringe 68b injects pressurized fluid into the inner member lumen 42 such that fluid flows through the inner member lumen 42, the passages 54, the balloon 46 and out through the inner member distal opening 43. The open-ended flow paths for injecting fluid into the catheter to purge air from the catheter allows confirmation that air has been successfully been purged from the catheter 10 by observing fluid flow out through the outer member distal opening 20 and the inner member distal opening 43.

Figure 4:
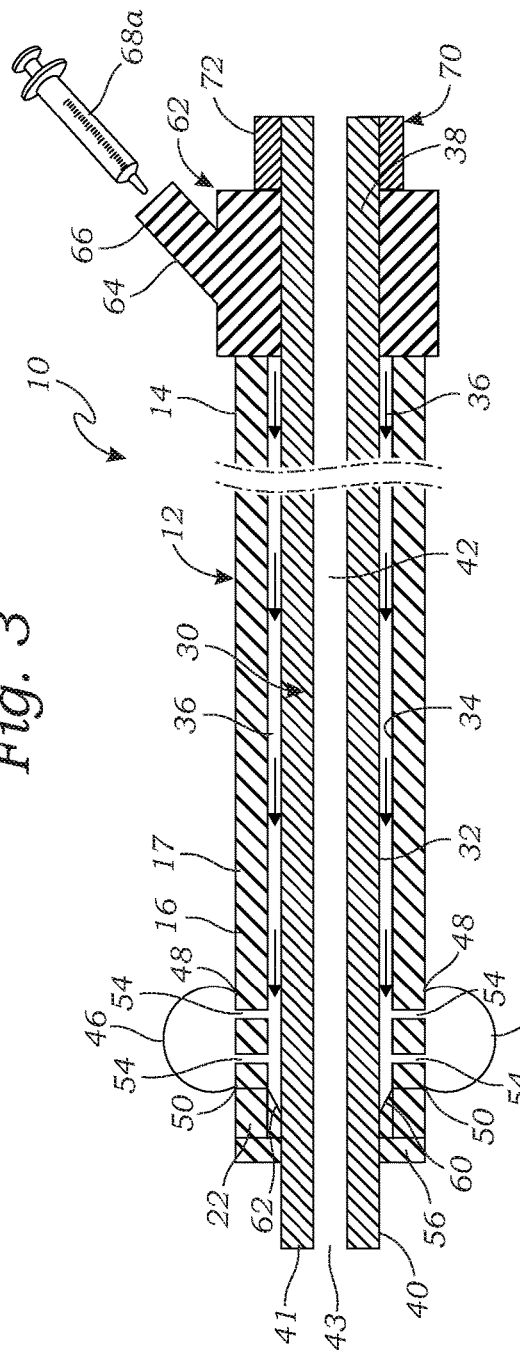
FIG. 4 is a side, cross-sectional view of the balloon guide catheter of FIG. 1, with the inner member in the sealing position and the balloon inflated, according to one embodiment of the present invention.

Referring to FIGS. 2, 3 and 4, when the inner member 30 is in the sealing position, the balloon 46 can be inflated by injecting pressurized fluid into the outer member lumen 18 via the fluid port 64 of the hub 62. With the inner member 30 in the sealing position, the annular fluid path 36 is sealed at a location distal of the inflation passages 54 such that pressurized fluid injected into annular fluid path 36 injects pressurized fluid into the balloon 46 through the inflation passages 54. The injected fluid flows through the annular fluid path 36 and the passages 54, respectively, into the balloon interior which inflates the balloon 46 as shown in FIG. 4. The balloon 46 may deflated by depressurizing the inflation fluid. In one way, the inflation fluid may be depressurized by aspirating through the syringe 68a, or simply relieving the pressure through the fluid port 64.

In another way, the balloon 46 may be quickly deflated by moving the moving the inner member 30 to the non-sealing position as shown in FIG. 1 (i.e., pulling the inner member 30 proximally relative to the outer member 12 thereby unsealing the passages 54 which allows the pressurized fluid in the balloon 46 to release into the outer member lumen 18. In another feature, the seal 56 may be configured such that it seals the outer member distal opening 20 when the inner member 30 is retracted within the outer member 12 such that the distal end 41 of the inner member is proximal to the seal 56.

Figure 5:
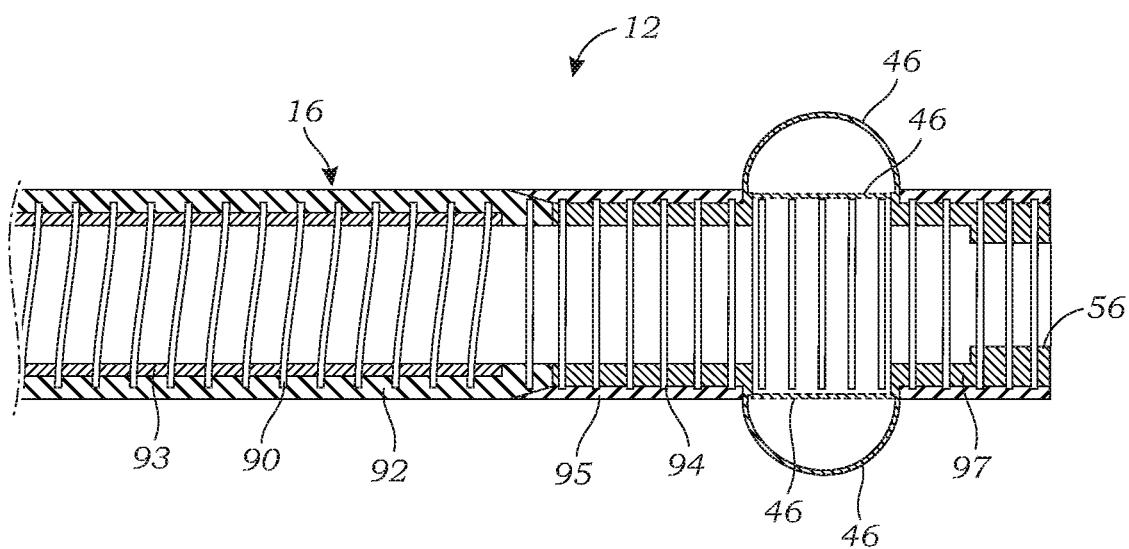
FIG. 5 is a side, cross-sectional view of the distal portion of the balloon guide catheter of FIG. 1 showing an alternative construction, according to one embodiment of the present invention.

FIG. 5 shows a more detailed view of an alternative configuration for the distal portion 16 of the outer member 12, the balloon 46 and the seal 56. The balloon 46 in the uninflated state is shown in dashed lines in FIG. 5. In this configuration, the outer member 12 comprises a proximal hypotube portion 90 formed of a stainless steel hypotube having a helical cut pattern. The proximal hypotube portion 90 has an external coating 92 covering the outside of the proximal hypotube portion 90. The external coating 92 may be any suitable material, such as a polymer like Pebax 35D. The external coating 92 may be applied by extruding the external coating 92 onto the proximal hypotube portion 90. The proximal hypotube portion 92 also has an internal coating 93 covering the inside of the proximal hypotube portion 90. The internal coating 93 is preferably a low-friction polymer material, such as PTFE (Teflon®) or other suitable polymer material. The internal coating 93 may also be applied to the proximal hypotube portion 90 by extruding the internal coating 93 onto the proximal hypotube portion 90. The distal portion 16 has a distal hypotube portion 94 attached to the distal end of the proximal hypotube portion 92. The distal hypotube portion 94 may be a stainless steel hypotube (which may be integral to the hypotube 90, or a separate hypotube attached to the hypotube portion 94, such as by welding) having a slotted cut pattern, for example. A tie layer 95 may then be applied to the outside surface of the distal portion of the proximal hypotube portion 90 and the proximal end of the distal hypotube portion 94. The tie layer 95 facilitates bonding the external coating 92 to the distal cover 97 (which integrally forms the balloon 46 and seal 56). For instance, the material forming the external coating 92 may not be compatible for bonding to the distal cover 97, so a tie layer is used which effectively bonds to both the external coating 92 and the distal cover 97. The tie layer may be formed of any suitable material, such as 95A EX TL LLDPE. The distal cover 97 is applied to the distal hypotube portion 94. In one process, the distal cover 97 may be formed from a thin tube which is slid over the distal hypotube portion 94. The distal cover 97 may be formed of any suitable material, preferably a material having a low hardness (less than 50 Shore A, such as Mediprene™, Chronoprene™, silicone, or Rezilient™). Then, the thin tube may be heated and/or melted, and formed using mandrels to form the seal 56, balloon 46 and the lumen of the outer tube 12 in the region of the distal cover. In one exemplary process, a first mandrel is installed within the distal hypotube portion 94 having a diameter to form the lumen of the outer tube 12. The thin tube is melted to form the lumen of the outer tube. Next, a second mandrel is installed at the distal end of the distal hypotube portion 94 to form the seal 56. The thin tube is melted in this area to form the seal 56. The thin tube may have a starting thickness suitable to form the balloon 46, and the thin tube in the length of the balloon 46 is left unattached from the distal hypotube portion 94 such that this portion can expand when inflation fluid is injected into the balloon.

As shown in FIG. 5, the balloon 46 (uniflated balloon 46 shown in dashed lines) has an outer diameter which is flush with the adjacent tie layer 95 when the balloon 46 is in the uninflated state. Accordingly, when the balloon 46 is uninflated, the balloon 46 does not form a bump or raised area relative to the outer surface of the adjacent portions of the outer member 12. Turning to FIG. 6, a method of using the balloon guide catheter 10 to perform a medical procedure for removing an embolus 80 in a blood vessel 82 will now be described. At Step A, the balloon guide catheter 10 is prepared for insertion into the vascular system of the patient by purging air from the balloon guide catheter 10. As shown in Step A of FIG. 6, the inner member 30 is positioned in the non-sealing position. The inner member 30 may be pre-positioned in the sealing position upon removal from its original, sterile packaging, or the inner member 30 may be moved relative to the outer member 12 to position the inner member 30 in the sealing position. As described above, the syringe 68a filled with flushing fluid (e.g., saline) is attached to the fluid port 64 and the syringe 68b filled with flushing fluid (e.g., saline) is attached to the fluid interface 72. The syringes 68a, 68b are actuated to inject the flushing fluid through the outer member lumen 18, annular fluid path 36, fluid passages 54, the balloon 46, and/or the inner member lumen 42 and out through the outer member distal opening 20 and inner member distal opening 43. When fluid is observed flowing out of the inner member distal opening and outer member distal opening (e.g., without air bubbles) the balloon guide catheter 10 has been successfully purged of air, and the balloon guide catheter 10 is now prepared for insertion into the vascular system of the patient.

At Step B of FIG. 6, the inner member 30 is moved distally relative to the outer member 12 to the sealing position such that the seal 56 contacts the outer surface 32 of the distal portion thereby sealing the annular fluid path 36. It should be understood that Step (b) may be performed before or after inserting the balloon guide catheter into the vascular system of the patient.

At Step C, the balloon guide catheter 10 is inserted into the vascular system of the patient and is advanced to a location proximate the embolus 80 (the treatment site) within the blood vessel 82 of the vascular system. For instance, the balloon guide catheter 10 is inserted through an entry incision into an entry blood vessel, such as the inferior vena cava or femoral artery near the groin. The balloon guide catheter 10 is advanced through the vascular system to position the balloon 46 within the blood vessel 82 proximate the embolus 80. The inner member 30 and outer member 12 may be advanced simultaneously, or separately, and at the same rate or different rates. The inner member 30 may be telescoped relative to the outer member 12 such that the distal portion 40 of inner member 30 extends past the distal end 22 of the outer member 12, thereby providing a more flexible distal tip to the guide catheter assembly 10. As explained above, the more flexible distal tip can make it easier to guide and manipulate the catheter 10 through vascular system, especially tortuous regions of the vascular system, such as the neurovascular.

At Step D of FIG. 6, with the balloon 46 positioned proximate the embolus 80 the balloon 46 is inflated with the inner member 30 positioned in the sealing position. To inflate the balloon 46, the syringe 68a filled with inflation fluid (e.g., saline) is attached to the fluid port 64 and is actuated to inject the inflation fluid through annular fluid path 36, through the one or more passages 54, and into the inflatable balloon interior. The inflated balloon 46 isolates the blood vessel 82 downstream of the balloon 46, including the location of the embolism from the flow of blood.

At Step E of FIG. 6, an embolus removal device 84 is inserted through the inner member lumen 42, and is advanced past the distal end 41 of the inner member 30 to grasp or otherwise capture the embolus 82. At Step F of FIG. 6, the embolus 82 is removed from the patient, and the balloon guide catheter 10 is removed from the patient. The embolus 82 may be removed by pulling the embolus removal device 82 with the captured embolus 82 proximally through the inner member lumen 42 and out of the patient. Alternatively, the inner member 30 may be pulled proximally along with the embolus removal device 82 with the captured embolus 82 and out of the patient. The inner member 30 may be pulled proximally while the outer member 12 is left in place within the patient. The outer member 12 may then continue to be used as a guide catheter, for example to advance other catheters or medical devices through the outer member 12.

In still another way, the balloon 46 is deflated by depressurizing the inflation fluid (e.g., by aspirating through the syringe 68a), and the embolus removal device 84 and balloon guide catheter 10 are retracted proximally from the blood vessel 82 to remove the embolus 80 from the blood vessel 82.

It is understood that the method of using the balloon guide catheter 10 depicted in FIG. 6, and described herein, is not limited to removing an embolus, but may be modified to perform any suitable medical procedure. For example, instead of removing an embolus, the method of FIG. 6 may be modified to insert a medical imaging device through the inner member lumen 42, and advanced past the distal end 41 of the inner member 30. The medical imaging device may then be used to image the treatment site. In other medical procedures, the balloon guide catheter 10 may be used for intravascular device implantation, or the like, as one of ordinary skill in art would appreciate.

Turning now to FIGS. 7-8 a second embodiment of a balloon guide catheter 100 for performing a procedure within a vascular system, such as treating ischemic strokes, and blocking or restricting blood flow for other treatment or diagnostic purposes, is shown. The balloon guide catheter 100, like the balloon guide catheter 10, is specially configured to allow for fast preparation for performing a surgical procedure, such as allowing fast and effective purging of air from the catheter 10. The balloon guide catheter 100 is similar to the balloon guide catheter 10, except that it has a seal 156 disposed circumferentially around an outside surface 32 of the distal portion 40 of the inner member 30, instead of on the inside surface of the outer member. Indeed, the balloon guide catheter 100 has many of the same elements as the balloon guide catheter 10, wherein like reference numerals refer to like elements and the description for like elements shall be applicable to both embodiments wherever relevant.

Same as, or similar to, the balloon guide catheter 10, the balloon guide catheter 100 has an elongated, flexible, tubular outer member 12, and an elongated, flexible, tubular inner member 30 disposed within the outer member lumen 18. The outer member 12 and inner member 30 of the balloon guide catheter 100 have the same or similar features as the balloon guide catheter 10. The distal portion 40 of the inner member 30 extends out through the distal opening 20 of the outer member 12.

The balloon guide catheter 100 also has a balloon 46 secured to and circumferentially disposed around the outer surface 17 of the distal portion 16 of the outer member 12. The outer member 12 has one or more conduits or passages 54 through the wall of the outer member 12 forming a fluid pathway between the annular fluid path 36 and the balloon interior 52.

The balloon guide catheter 100 has an elastomeric, tubular seal 156 disposed circumferentially around the outside surface 32 of the distal portion 40 of the inner member 30. The seal 156 is configured to form a fluid tight seal between the inside surface 34 of the outer member 12 and the outer surface 32 of the inner member 30. While the seal 156 may have ant suitable shape and configuration, the seal 156 shown in FIGS. 7-8 has a conical outer surface which tapers from a smaller proximal end 157 to a larger distal end 159 having a larger diameter than the proximal end. The conical shape of the seal 156 facilitates the seal 156 inserting into the distal opening 20 of the outer member 12 when the inner member 30 is moved proximally relative to the outer member 12 thereby moving the seal 156 proximally into the distal opening 20 of the outer member 12.

The balloon guide catheter 100 has a distal stop 190 on the distal end 41 of the inner member 30 located distal of the distal end 58 of the outer member 12 such that the stop 190 prevents the distal end 41 of the inner member 30 from being moved proximally past the distal end 58 of the outer member 30.

The inner member 30 is movable longitudinally relative to the outer member 12 from a non-sealing position (as shown in FIG. 7) in which the seal 156 is positioned distal to the outer member distal opening 20, and a sealing position (as shown in FIG. 8) in which the seal 156 is positioned within the outer member lumen 18 such that the seal 156 contacts the inside surface 34 of the outer member 12 thereby sealing the annular fluid path 36. In the sealing position, the distal stop 190 may bear against the distal end 58 of the outer member 12.

As shown in FIG. 7, in the non-sealing position of the inner member 30, the seal 156 is located distally of the outer member distal opening 20, such that the seal does not contact the outer member 12. Referring to FIG. 7, the inner member 30 has been moved longitudinally in the proximal direction relative to the outer member 12 to the sealing position such that the seal 156 is inserted into the outer member distal opening 20. When the inner member is in the sealing position as shown in FIG. 7, the seal 156 seals the annular fluid path 36 at the location of the seal 56.

Referring to FIG. 7, with the inner member 30 in the non-sealing position, air may be easily purged from the balloon guide catheter 100 because there is an open fluid pathway from the proximal portions 38, 14 and the distal openings 43, 20 of the inner member 30 and outer member 12, respectively. Air is purged from the balloon guide catheter 100 by introducing pressurized fluid through the outer member lumen 18 via the fluid port 64 of the hub 62 and through the inner member lumen 42 via the fluid interface 70. As shown in FIG. 6, the syringe 68a filled with fluid, such as saline, is attached to the Luer lock 66 of the fluid port 64. The syringe 68a is then used to inject pressurized fluid into the outer member lumen 18 such that fluid flows through the annular fluid path 36, the outer member lumen 18, the passages 54, the balloon 46 and out through the outer member distal opening 20. Similarly, the syringe 68b filled with fluid, such as saline, is attached to the Luer lock 72 of the fluid interface 70. The syringe 68b injects pressurized fluid into the inner member lumen 42 such that fluid flows through the inner member lumen 42, the passages 54, the balloon 46 and out through the inner member distal opening 43. The open-ended flow paths for injecting fluid into the catheter to purge air from the catheter allows confirmation that air has been successfully been purged from the catheter 100 by observing fluid flow out through the outer member distal opening 20 and the inner member distal opening 43.

As shown in FIG. 8, with the inner member 30 in the sealing position, the annular fluid path 36 is sealed at a location distal of the inflation passages 54 such that pressurized fluid injected into annular fluid path 36 injects, pressurized fluid into the balloon 46 through the inflation passages 54. As shown in FIG. 8, a syringe 68a is attached to the fluid port 64 and the syringe 68a is actuated to inject inflation fluid which flows the annular fluid path 36 and the passages 54, respectively, into the balloon interior which inflates the balloon 46.

Like the balloon guide catheter 10, the inner member 30 may be moved distally such that a desired amount of the distal portion 40 of the inner member 30 extends distally past the distal end 22 of the outer member 12. In this way, the distal portion 40 of the inner member 30 extending distally of the distal end 22 provides a more flexible distal end of the guide catheter assembly 10. This more flexible distal tip can facilitate guiding and manipulating the catheter 100 through the vascular system, such as through tortuous regions like the neurovascular blood vessels.

The balloon 46 of the balloon guide catheter 100 may deflated by depressurizing the inflation fluid. In one way, the inflation fluid may be depressurized by aspirating through the syringe 68a, or simply relieving the pressure through the fluid port 64. Alternatively, the balloon 46 may be quickly deflated by moving the moving the inner member 30 to the non-sealing position as shown in FIG. 7 (i.e., pushing the inner member 30 distally relative to the outer member 12) thereby unsealing the annular fluid path 36 and the passages 54 which allows the pressurized fluid in the balloon 46 to release past the distal end of the annular fluid path 36.

The method of using the balloon guide catheter 100 is substantially the same as the method of using the balloon guide catheter 10, as described above with reference to FIG. 6, except that the process of moving the inner member 30 between the sealing and non-sealing positions is different, as described herein. Accordingly, the description of the method depicted in FIG. 6 applies equally to the method of using the balloon guide catheter 100, except for the differences in adjusting the inner member 30 between the non-sealing and sealing positions.

Similar to the flush construction of the balloon 46 as shown in FIG. 5, the balloon guide catheters 10 and 100 may also be configured such that the uninflated balloon 46 is substantially flush with, or does not protrude radially beyond, the adjacent outer surface of the outer member 12. For example, FIGS. 9A-9B illustrate another embodiment of a balloon guide catheter 200 which is the same as the balloon guide catheter 10 except that the outside diameter of the outer member 12 in the area of the balloon 46 may have a reduced diameter so as to form a recess 47 (or pocket 47) extending the length of the outer member 12 from the proximal end 48 of the balloon 46 to the distal end 50 of the balloon 46. Hence, when the balloon 46 is in the uninflated state, the balloon 46 is substantially flush with the outside surface of the outer member 12 adjacent the balloon 46. The balloon guide catheter 200 and its operation are the same as the balloon guide catheter 10.

The balloon guide catheter 100 may also have a recess or pocket same or similar to the recess 47 shown in FIGS. 9A-9B. Again, such balloon guide catheter and its operation are the same as the balloon guide catheter 200.

Although particular embodiments have been shown and described, it is to be understood that the above description is not intended to limit the scope of these embodiments. While embodiments and variations of the many aspects of the invention have been disclosed and described herein, such disclosure is provided for purposes of explanation and illustration only. Thus, various changes and modifications may be made without departing from the scope of the claims. For example, not all of the components described in the embodiments are necessary, and the invention may include any suitable combinations of the described components, and the general shapes and relative sizes of the components of the invention may be modified. While the systems and methods have been described cytological samples, they can be configured and utilized with any types of samples. Accordingly, embodiments are intended to exemplify alternatives, modifications, and equivalents that may fall within the scope of the claims. The invention, therefore, should not be limited, except to the following claims, and their equivalents.

What is claimed is:

1. A method of using a balloon catheter assembly, the balloon catheter assembly comprising,
a tubular outer member having a proximal portion, a distal portion, and an outer member lumen extending there between, wherein the outer member lumen is in communication with a distal opening of the outer member,
a tubular inner member having a proximal portion, a distal portion, and an inner member lumen extending there between, wherein the inner member lumen is in communication with a distal opening of the inner member, the inner member being at least partially disposed in the lumen of the outer member such that an outer surface of the inner member and an inner surface of the outer member together define an annular fluid path,
a balloon member having respective proximal and distal ends secured to and circumferentially around an outer surface of the distal portion of the outer member such that an inner surface of the balloon member and the outer surface of the outer member define an inflatable balloon interior, the outer member comprising a wall having one or more passages therethrough that form a fluid pathway between the annular fluid path and the balloon interior, and
a tubular seal disposed circumferentially around the inner surface of the distal portion of the outer member distal of the one or more passages, wherein the seal is configured to form a fluid tight seal between the inner surface of the outer member and the outer surface of the inner member,
wherein the inner member is movable relative to the outer member from a non-sealing position in which the distal portion of the inner member is positioned proximal of the seal, and a sealing position in which the distal portion of the inner member contacts the seal thereby sealing the annular fluid path at the location of the seal;
the method comprising:
with the inner member positioned in the non-sealing position, purging air from one or more of the outer member lumen, inner member lumen, one or more passages, annular flow path and balloon interior, respectively, by introducing fluid through the inner member lumen and outer member lumen so that the introduced fluid flows out the respective inner member distal opening and outer member distal opening;
inserting the catheter assembly into a vascular system;
advancing the inner member and outer member through the vascular system to position the balloon member proximal to a treatment site;
with the inner member positioned in the sealing position, inflating the balloon interior by introducing fluid into the outer member lumen such that the fluid flows through the annular fluid path, through the one or more passages, and into the balloon interior.

2. The method of claim 1, wherein when the balloon interior is inflated, the balloon member seals a lumen of the vascular system proximal to the treatment site.

3. The method of claim 1, wherein air is purged from one or more of the inner member lumen, outer member lumen, annular fluid path, one or more passages and balloon interior, respectively, prior to inserting the inner member and outer member into the vascular system.

4. The method of claim 1, wherein the catheter assembly is inserted into the vascular system and advanced through the vascular system with the inner member in the non-sealing position, the method further comprising
prior to inflating the balloon interior, moving the inner member relative to the outer member from the non-sealing position to the sealing position.

5. The method of claim 1, further comprising
before or while inserting the inner member and outer member into the vascular system and advancing the inner member and outer member through the vascular system, moving the inner member relative to the outer member such that the inner member extends through the seal and beyond a distal end of the outer member.

6. The method of claim 1, wherein air is purged from one or more of the inner member lumen, outer member lumen, annular fluid path, one or more passages, and balloon interior, respectfully, after inserting the inner member and outer member into the vascular system.

7. The method of claim 6, further comprising moving the inner member relative to the outer member from the non-sealing position to the sealing position prior to inflating the balloon interior.

8. The method of claim 1, further comprising moving the inner member relative to the outer member to the non-sealing position prior to purging air from one or more of the inner member lumen, outer member lumen, annular fluid path, one or more passages, and balloon interior.

9. The method of claim 1, further comprising
after inflating the balloon interior, moving the inner member distally relative to the outer member such that the inner member extends through the seal and beyond a distal end of the outer member.

10. The method of claim 1, further comprising deflating the balloon interior by moving the inner member to the non-sealing position.

* * * * *